(12) United States Patent
Moghimi et al.

(10) Patent No.: US 11,857,272 B2
(45) Date of Patent: Jan. 2, 2024

(54) IMPLANTED ARTICLE PHYSICAL REFERENCING APPARATUS

(71) Applicant: SI-Restore LLC, Austin, TX (US)

(72) Inventors: Michael Hoomani Moghimi, Austin, TX (US); Daniel Brian Lanois, Prosper, TX (US)

(73) Assignee: SI-RESTORE LLC, Austin, TX (US)

( * ) Notice: Subject to any disclaimer, the term of this patent is extended or adjusted under 35 U.S.C. 154(b) by 369 days.

(21) Appl. No.: 17/321,644

(22) Filed: May 17, 2021

(65) Prior Publication Data

US 2022/0361953 A1 Nov. 17, 2022

(51) Int. Cl.
| | |
|---|---|
| *A61B 17/70* | (2006.01) |
| *A61B 34/20* | (2016.01) |
| *A61B 17/34* | (2006.01) |
| *A61B 17/17* | (2006.01) |

(52) U.S. Cl.
CPC .......... *A61B 34/20* (2016.02); *A61B 17/1717* (2013.01); *A61B 17/3468* (2013.01); *A61B 17/7082* (2013.01); *A61B 17/1742* (2013.01); *A61B 17/1757* (2013.01); *A61B 2017/3405* (2013.01); *A61B 2017/347* (2013.01); *A61B 2034/2068* (2016.02)

(58) Field of Classification Search
CPC . A61B 34/20; A61B 17/1717; A61B 17/3468; A61B 17/7082; A61B 17/1742; A61B 17/1757; A61B 2034/2068; A61B 2017/3405; A61B 2017/347
USPC ...................................................... 606/53, 59
See application file for complete search history.

(56) References Cited

U.S. PATENT DOCUMENTS

| | | | | |
|---|---|---|---|---|
| 4,360,012 A | * | 11/1982 | McHarrie | A61B 17/6441 606/54 |
| 4,869,242 A | * | 9/1989 | Galluzzo | A61B 17/66 411/476 |
| 6,171,307 B1 | * | 1/2001 | Orlich | A61B 17/66 606/53 |
| 7,881,771 B2 | * | 2/2011 | Koo | A61B 17/6416 606/53 |
| 8,372,074 B2 | * | 2/2013 | Milbank | A61B 17/7208 606/62 |
| 10,772,639 B2 | * | 9/2020 | Wu | A61B 17/1764 |
| 2002/0165552 A1 | | 11/2002 | Duffner | |

(Continued)

*Primary Examiner* — Eduardo C Robert
*Assistant Examiner* — David C Comstock
(74) *Attorney, Agent, or Firm* — David O. Simmons; IVC Patent Agency

(57) ABSTRACT

An implanted article physical referencing apparatus comprises a guide body, a first guide shaft and a second guide shaft. The guide body includes a plurality of guide shaft receptacles therein. A longitudinal axis of each of the guide shaft receptacles extends substantially parallel to a longitudinal reference axis of the guide body. The first and second guide shafts each have a proximate end portion and a distal end portion. The proximate end portion of the first guide shaft includes an exterior surface adapted for being engaged with a corresponding interior surface of a selected one of the guide shaft receptacles to constrain unrestricted relative movement between the first guide shaft and the guide body. The proximate end portion of the second guide shaft is attached to the guide body. A longitudinal axis of the second guide shaft extends substantially parallel to the longitudinal reference axis of the guide body.

19 Claims, 4 Drawing Sheets

(56) References Cited

U.S. PATENT DOCUMENTS

| | | | |
|---|---|---|---|
| 2005/0261680 A1* | 11/2005 | Draper | A61B 17/6425 606/59 |
| 2006/0052795 A1 | 3/2006 | White | |
| 2006/0155276 A1* | 7/2006 | Walulik | A61B 17/6441 606/59 |
| 2006/0167454 A1 | 7/2006 | Ludwig et al. | |
| 2008/0015603 A1* | 1/2008 | Collazo | A61B 17/157 606/87 |
| 2009/0118733 A1 | 5/2009 | Orsak et al. | |
| 2013/0261670 A1* | 10/2013 | Laeng | A61B 17/025 606/281 |
| 2014/0081267 A1* | 3/2014 | Orsak | A61B 17/8875 606/59 |
| 2015/0238203 A1 | 8/2015 | Asfora | |
| 2015/0342652 A1 | 12/2015 | Orbay et al. | |
| 2018/0146994 A1* | 5/2018 | Biedermann | A61B 17/8061 |
| 2018/0333277 A1 | 11/2018 | Finkel et al. | |

\* cited by examiner

IMPLANTED ARTICLE PHYSICAL REFERENCING APPARATUS

FIELD OF THE DISCLOSURE

The disclosures made herein relate generally to devices used in surgical procedures and, more particularly, to an apparatus used for determining the position of a target implanted article location relative to a reference implanted article location.

BACKGROUND

It is well known that surgical procedures often require one or more implant articles to be placed (i.e., installed) into the body of a patient. For example, orthopedic surgical procedures often include placement of one or more bone screws into a bony structure of a patient. Spinal vertebrae and the pelvic bone are non-limiting.

examples of such bony structure of a patient into which an implanted article such as a bone screw may be placed.

There are a host of techniques available for facilitating the placement of implanted articles into the bony structure of a patient. Placement of implanted articles utilizing radiographic imaging such as fluoroscopy, computed tomography (CT) and the like are well-known and have their respective utility and beneficial attributes. Similarly, placement of implanted articles utilizing physical referencing from a known location of the bony structure of a patient is also well-known and has its respective utility and beneficial attributes. For example, after an implanted articles or locating structure for placing an implanted article (e.g., a Steinmann pin) is placed using a radiographic imaging technique, placement of one or more subsequent instances of such implanted articles and/or locating structure therefor may be implemented using physical referencing from the previously placed implanted article and/or locating structure therefor.

A benefit of utilizing physical referencing for placement of implanted articles and/or locating structure therefor is accuracy relative to a previously placed implanted article and/or locating structure therefor. For example, once a first instance of an implanted article locating structure is placed using radiographic imaging, one or more subsequent instances of the implanted article locating structure can be placed using physical referencing. Such physical referencing utilizes a given dimensional distance between a reference location (e.g., location of an implanted article locating structure placed using radiographic imaging) and a target location (e.g., location of a subsequently placed implant article). In this manner, physically referencing from a reference location to a target location provides a simple and efficient means of accurately placing an implant article at a target location relative to a previously placed implanted article and/or locating structure therefor (i.e., the reference location).

Although prior art implementations of implant article placement guides are known, they are also known to suffer from various drawbacks that limit their utility and beneficial attributes. One such drawback is that some prior art implementations of implant article placement guides are configured in a manner that limits or precludes their use in some types of surgical procedures. For example, some prior art implementations of implant article placement guides have a structure that precludes their use in minimally-invasive procedures (e.g., spine fixation and the like). Another such drawback is that some prior art implementations of implant article placement guides are configured in manner that requires a set of such guides to accommodate common and expected differences in patient anatomy (e.g., depth of surgical site associated with body fat and/or body volume). Still another such drawback is that some prior art implementations of implant article placement guides are configured in manner that can contribute to human error in the accuracy of an intended dimensional distance provided for by the guide. For example, some prior art implementations of implant article placement guides have an adjustment mechanism that relies entirely or predominately upon human interaction for achieving an intended dimensional distance.

Therefore, an implant article placement guide that overcomes drawbacks associated with prior art implant article placement guides would be advantageous, desirable and useful.

SUMMARY OF THE DISCLOSURE

Embodiments of the present invention are directed to a variable implant article placement guide (i.e., an implanted article physical referencing apparatus) for use in surgical procedures. Advantageously, a variable implant article placement guide in accordance with one or more embodiments of the present invention overcomes drawbacks that limit utility and beneficial attributes of prior art variable implant article placement guides. To this end, a variable implant article placement guide in accordance with one or more embodiments of the present invention is configured in a manner that enables its use in minimally-invasive procedures, that enables a single guide to be useful even where expected differences in patient anatomy exist (e.g., depth of surgical site associated with body fat and/or body volume) and that limits the potential for human error in achieving accuracy of an intended dimensional distance between placed implant articles.

In one embodiment of the present invention, an implanted article physical referencing apparatus (e.g., a variable implant article placement guide) comprises a guide body and a first guide shaft. The guide body includes a plurality of guide shaft receptacles therein. A longitudinal axis of each of the guide shaft receptacles extends substantially parallel to a longitudinal reference axis of the guide body. The first guide shaft has a proximate end portion and a distal end portion. The proximate end portion of the first guide shaft includes an exterior surface adapted for being engaged with a corresponding interior surface of a selected one of the guide shaft receptacles to constrain unrestricted relative movement between the first guide shaft and the guide body.

In another embodiment of the present invention, a variable implant article placement guide assembly comprises a guide body, a first guide shaft and a second guide shaft. The guide body includes a reference location guide shaft receptacle therein and a plurality of target location guide shaft receptacles therein. A longitudinal axis of all of the guide shaft receptacles extends substantially parallel to a longitudinal reference axis of the guide body. Each of the target location guide shaft receptacles is spaced-apart from each adjacent one of the target location guide shaft receptacles. The reference location guide shaft receptacle is spaced away from all of the target location guide shaft receptacles. The first guide shaft has a proximate end portion and a distal end portion. The proximate end portion of the first guide shaft includes an exterior surface engaged with any selected one of the target location guide shaft receptacles to constrain unrestricted relative movement between the first guide shaft and the guide body. The second guide shaft has a proximate end portion and a distal end portion. The proximate end portion of the second guide shaft is engaged with the reference location guide shaft receptacle to constrain unrestricted relative movement between the second guide shaft and the guide body. A longitudinal axis of the second guide shaft is the longitudinal reference axis of the guide body.

In one or more embodiments, a guide shaft lock can be provided that has a guide body engaging portion engaged with the guide body to constrain relative movement between the guide shaft lock and the guide body in a direction perpendicular to the longitudinal reference axis of the guide body and that has a first guide shaft engaging portion is engaged with the first guide shaft to constrain relative movement between the guide body and the first guide shaft in a direction generally parallel to the longitudinal reference axis of the guide body when the first guide shaft is engaged with any of the guide shaft receptacles.

In one or more embodiments, a second guide shaft can be attached to the guide body with a longitudinal axis thereof extending substantially parallel to the longitudinal reference axis of the guide body.

In one or more embodiments, the longitudinal axis of each of the guide shaft receptacles can lie on a transverse reference axis of the guide body.

In one or more embodiments, two or more of the guide shaft receptacles can intersect each other.

In one or more embodiments, two or more of the target location guide shaft receptacles can intersect each other.

In one or more embodiments, each of the guide shaft receptacles can have a structure that engages a mating structure of the first guide shaft when the first guide shaft is seated in a selected one of the guide shaft receptacles for constraining axial displacement of the first guide shaft relative to the guide body (i.e., defining a maximum insertion depth of the guide shaft relative to the guide body).

These and other objects, embodiments, advantages and/or distinctions of the present invention will become readily apparent upon further review of the following specification, associated drawings and appended claims.

DETAILED DESCRIPTION

Figure 1:
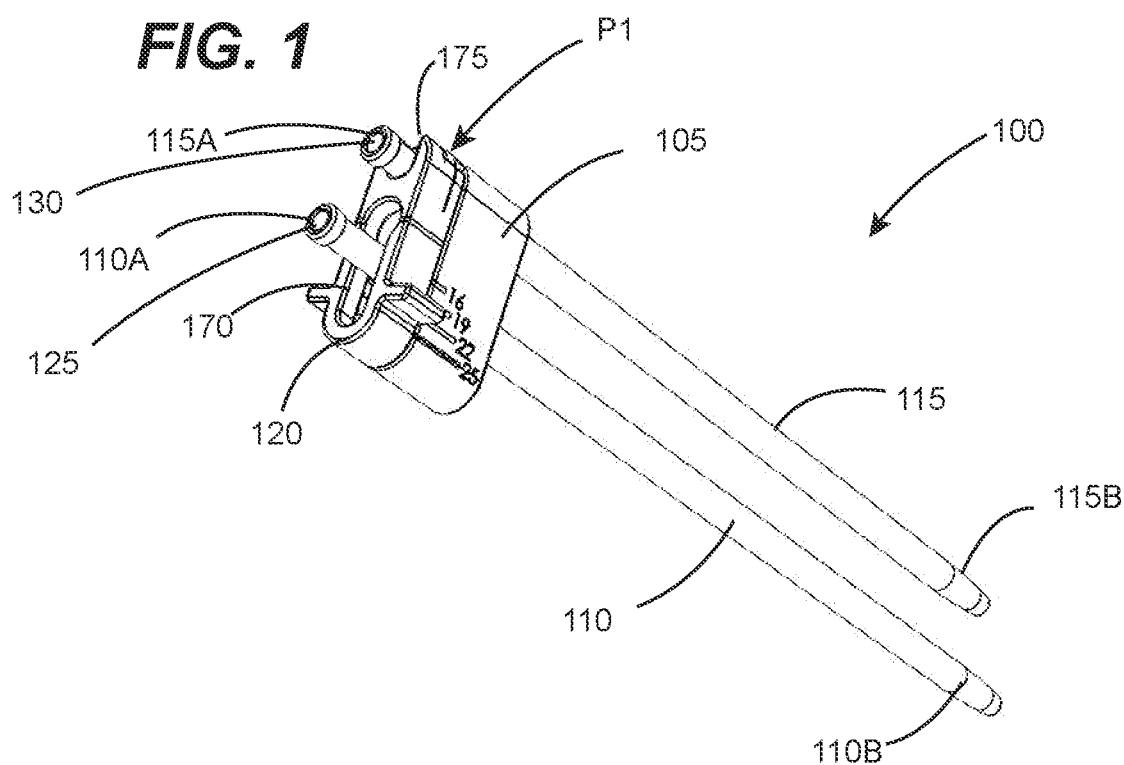
FIG. 1 is a perspective view showing an implanted article physical referencing apparatus in accordance with an embodiment of the present invention, with a guide member lock body thereof in a lock position thereof.
Figure 2:
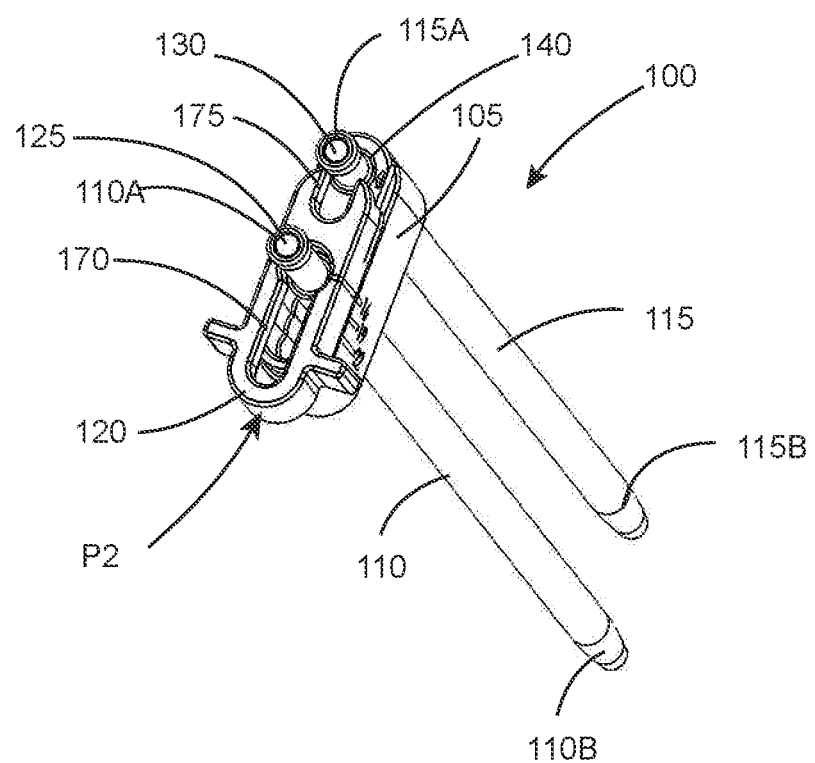
FIG. 2 is a top perspective view showing the implanted article physical referencing apparatus of FIG. 1, with a guide member lock body thereof in an unlock position thereof.
Figure 3:
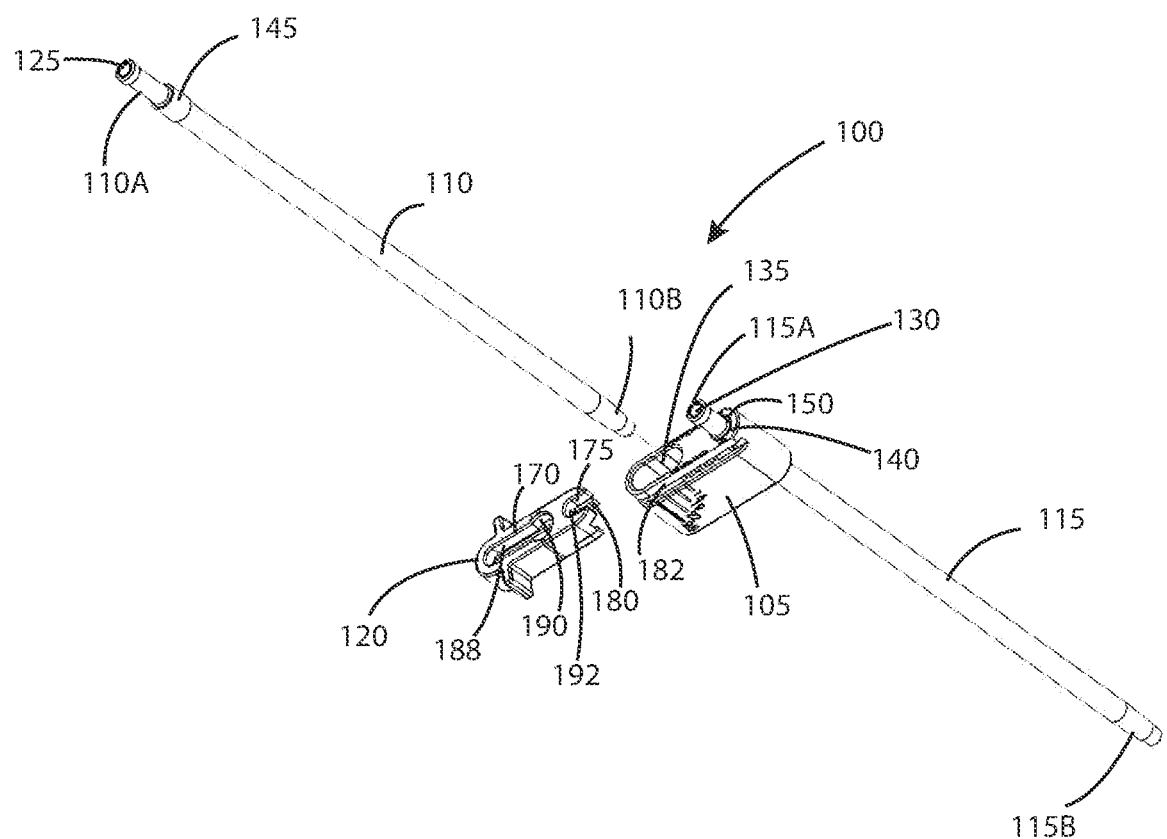
FIG. 3 is a partial assembly view of the implanted article physical referencing apparatus of FIG. 1.

FIGS. 1-3 show an implanted article physical referencing apparatus 100 configured in accordance with an embodiment of the present invention. The implanted article physical referencing apparatus 100 is an example of a variable implant article placement guide assembly configured in accordance with one or more embodiments of the present invention. The implanted article physical referencing apparatus 100 provide utility in surgical procedures in a manner that overcomes drawbacks that limit utility and beneficial attributes of prior art variable implant article placement guides. More specifically, the implanted article physical referencing apparatus 100 enables its use in minimally-invasive procedures, enables a single guide to be useful even where expected differences in patient anatomy exist (e.g., depth of surgical site associated with body fat and/or body volume) and limits the potential for human error in achieving accuracy of an intended dimensional distance between placed implant articles.

The implanted article physical referencing apparatus 100 includes a guide body 105, a first guide shaft 110, a second guide shaft 115 and a guide body lock 120. As discussed below in greater detail, the first guide shaft 110 and the second guide shaft 115 are attached to the guide body 105 in a spaced apart manner. In preferred embodiments, the first guide shaft 110 is movable between a plurality of spaced apart positions on the guide body 105 for enabling distance between implanted articles or locating structure for placing an implanted article (e.g., a Steinmann pin) to be selectively adjusted between a plurality of discrete guide shaft positions. The lock body 120 can be used to inhibit unrestricted axial movement of the first and second guide shafts 110, 115 relative to the guide body 105. In contrast to prior art devices, adjustment of the first guide shaft between a plurality of discrete location is advantageous relative to infinite adjustability over a provided range of adjustment.

The first and second guide shafts 110, 115 each have a central passage 125, 130 that extends at least partially through the first and second guide shafts 110, 115 along the respective longitudinal axis L1, L2 thereof. In preferred embodiments, the central passages 125, 104 of the first and second guide shafts 110, 115 extends through an entire length thereof. When the first and second guide shafts 110, 115 are mounted on the guide body 105 (e.g., when the implanted article physical referencing apparatus 100 is in use), the longitudinal axis L1 of the first guide shaft 110 extends substantially parallel to the longitudinal axis L2 of the second guide shaft 115.

Figure 4:
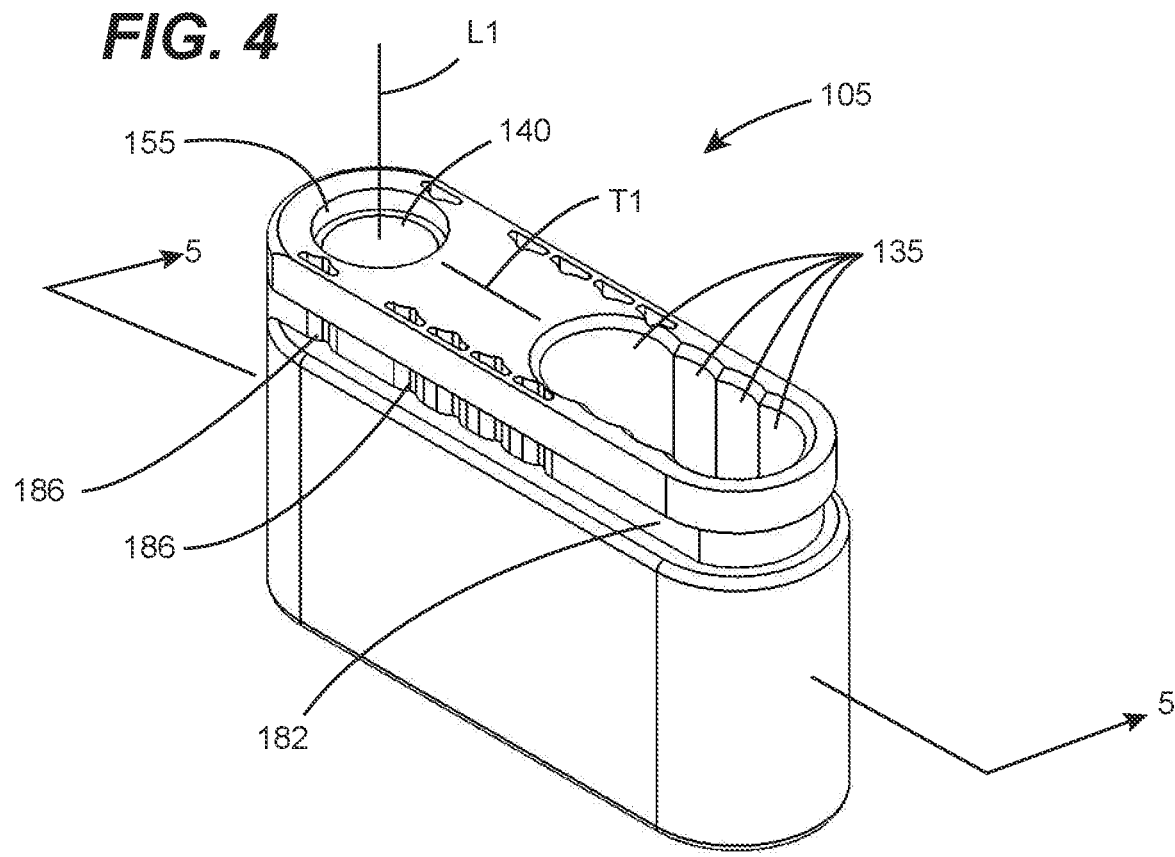
FIG. 4 is a perspective view showing a guide body of the implanted article physical referencing apparatus of FIG. 1.
Figure 5:
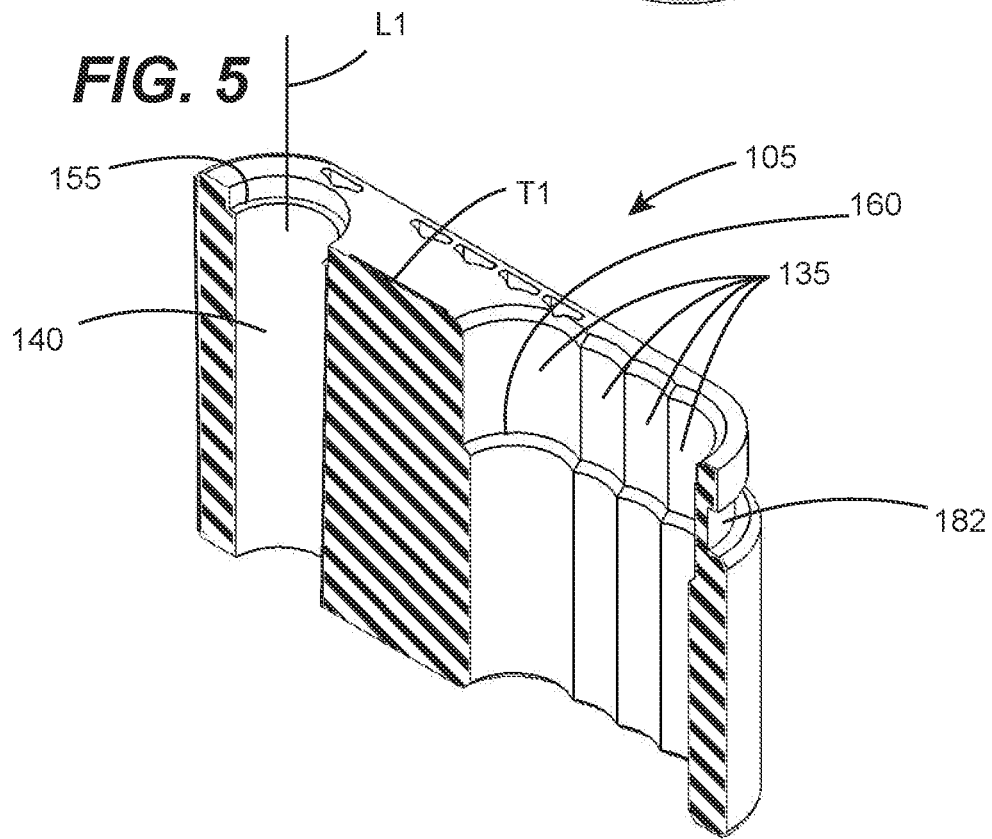
FIG. 5 is a cross-sectional view taken along the line 5-5 in FIG. 4.

As best shown in FIGS. 3-5, the guide body 105 includes a plurality of target location guide shaft receptacles 135 and a reference location guide shaft receptacle 140 and. A longitudinal axis of all of the guide shaft receptacles extends substantially parallel to a longitudinal reference axis L1 of the guide body 105. Each of the target location guide shaft receptacles 135 is spaced-apart from each adjacent one of the target location guide shaft receptacles 135. The reference location guide shaft receptacle 140 can be spaced away from all of the target location guide shaft receptacles 135. In one or more embodiments, as shown, the longitudinal axis of each of all of the guide shaft receptacles 135, 140 lie on a transverse reference axis T1 of the guide body and two or more of the target location guide shaft receptacles 140 (e.g., all of the target location guide shaft receptacles 140) intersect each other.

The first and second guide shafts 110, 115 each have a proximate end portion 110A, 115A and a distal end portion 110B, 115B. The proximate end portion 110A of the first guide shaft 110 and the proximate end portion 115A of the second guide shaft 115 each include an exterior surface engaged with any selected one of the target location guide shaft receptacles 140. To this end, the proximate end portion 110A of the first guide shaft 110 is configured to constrain unrestricted relative movement between the first guide shaft and the guide body. For example, as shown in FIG. 3, the first and second guide shafts 110, 115 can each include a cylindrical sidewall 142, 143 having a shoulder 145, 150 extending therefrom. The target location guide shaft receptacles 135 and the reference location guide shaft receptacle 140 can be configured mating structure such as a cylindrical, stepped sidewall passages that receive the respective one of the guide shafts 110, 115. The cylindrical, stepped sidewall passages of each of the shaft receptacles 135, 140 can include a shoulder 155,160 that is matingly engaged by the shoulder 145, 150 for limiting unrestricted axial displacement of the guide shafts 110, 115 relative to the guide body 105. In one or more embodiments, as best shown in FIGS. 4 and 5, the guide shafts 110, 115 each have a cylindrical side wall and the shaft receptacles 135, 140 each have a mating cylindrical side wall.

It is desirable to secure the first and second guide members 110, 115 in their seated positions relative to the guide body 105 to provide fixed position relative to each other and relative to the guide body 105. In one or more embodiments, the guide shaft lock 120, guide body 105 and guide shafts 110, 115 can be jointly configured for securing the first and second guide members 110, 115 in their seated positions relative to the guide body 105. In one of more other embodiments, the guide body 105 and guide shafts 110, 115 can be jointly configured with mating structures (e.g., interlocking protrusions and/or groves, interference fit, snap fit, or the like) for securing the first and second guide members 110, 115 in their seated positions relative to the guide body 105 without the use of the guide shaft lock 120.

Figure 6:
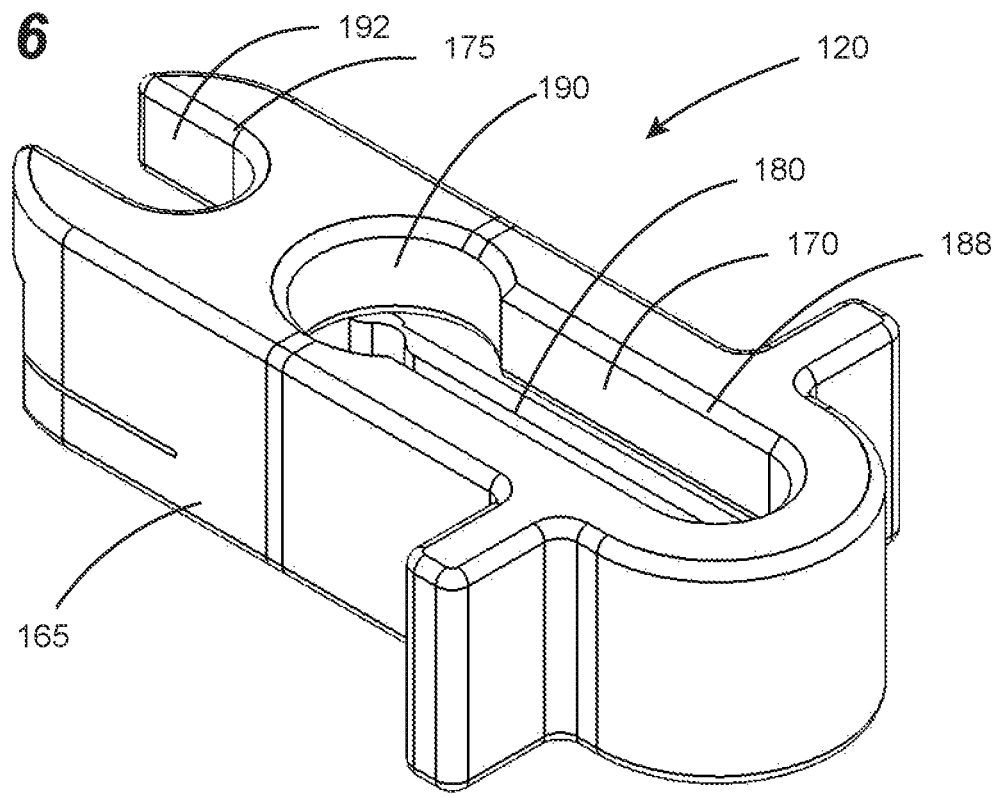
FIG. 6 is a top perspective view showing a guide body lock of the implanted article physical referencing apparatus of FIG. 1.
Figure 7:
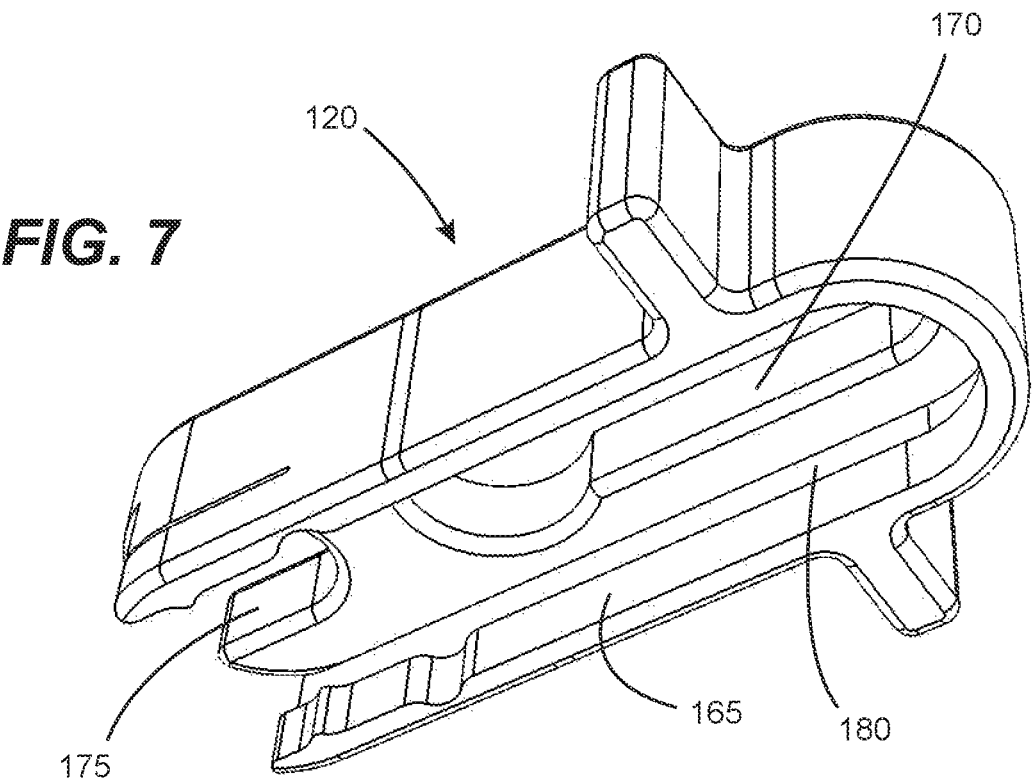
FIG. 7 is a bottom perspective view showing the guide body lock of the implanted article physical referencing apparatus of FIG. 1.

In a preferred embodiment, as shown in FIGS. 3 and 6-7, the guide shaft lock 120 has a guide body engaging portion 165, a first guide shaft engaging portion 170 and a second guide shaft engaging portion 175. The guide body engaging portion 165 engages a mating portion of the guide body 105 to constrain relative movement between the guide shaft lock and 120 the guide body 105 (e.g., in a direction along the longitudinal reference axis L1 of the guide body 105). In one or more embodiments, as shown, the guide body engaging portion 165 includes an elongated protrusion 180 that engages a mating groove 182 of the guide body 105. As best shown in FIGS. 3, 4, 7 and 8, the guide body engaging portion 165 can include one or more retention members (e.g., one or more projection 184) that engage a mating structure of the guide body (e.g., one or more recesses 186) for inhibiting limiting unrestricted movement guide body lock 120 relative to the guide body 105.

In one embodiment, as best shown in FIGS. 6 and 7, the first guide shaft engaging portion 170 includes an elongated aperture 188 with an intersecting shoulder passage 190 and the second guide shaft engaging portion 175 includes an open-ended aperture 192. Though engagement of the guide body engaging portion 165 with the mating portion of the guide body 105, the guide lock 120 can be moved (e.g., slid) along a length of the guide body 105 between a guide shaft insertion position P2 (FIG. 2) and a lock position P1 (FIG. 1). In the guide shaft insertion position P2 (FIG. 2), the shoulder passage 190 is aligned with a selected one of the target location guide shaft receptacles 135 for allowing the first guide shaft 110 to be seated in the selected on of the target location guide shaft receptacles 135 and (to the extent necessary) for allowing the second guide shaft 115 to be seated in the reference location guide shaft receptacle 140. When seated in the reference location guide shaft receptacle 140, a longitudinal axis of the second guide shaft 115 extends substantially colinear with the longitudinal reference axis L1 of the guide body 105. Moving the guide body lock to the lock position P1 (FIG. 1) causes the shoulders 145, 150 to become trapped under a respective overlying portion of the first and second guide shaft engaging portions 170, 175, thereby constraining relative movement between the guide body 105 and the first and second guide shafts 110, 115 in a direction along the longitudinal reference axis L1 of the guide body 105 to prevent the first and second guide shafts 110, 115 from becoming unseated from within the respective guide shaft receptacle 135, 140.

In use, the guide body lock 120 is engaged with the guide body 105 such that the intersecting shoulder passage 190 is aligned with a selected one of the target location guide shaft receptacles 135 of the guide body 105. The first guide shaft 110 can then be inserted into the selected on of the target location guide shaft receptacles 135 and the second guide shaft 115 can be inserted into the reference location guide shaft receptacle 140. The guide shafts 110, 115 are each inserted to a seated position at which the shoulder 145, 150 thereof engages the shoulder 155,160 of the respective shaft receptacle 135, 140, as shown in FIG. 2. In the seated position, the guide shafts 110, 115 are in a fixed position relative to the guide body 105. The guide body lock is then moved to the lock position P2, as shown in FIG. 1.

Advantageously, embodiments of the present invention can permit the guide shafts 110, 115 to be selected from a respective set of guide shafts having different configuration (e.g., length, exterior diameter, etc.). The selected guide shafts be inserted in the respective guide shaft receptacle 135, 140 (before and/or during a surgical procedure) for use with the guide body 105 and secured in place using the guide body lock (or other retention means). Alternatively, in one or more embodiments, the first guide shaft 110 and/or the second guide shaft 115 can be double ended with respect to the respective shoulder 145, 150 such that insertion from a first end provides a first effective guide shaft length and insertion from a second end provides a second effective guide shaft length.

Components of implanted article physical referencing apparatuses configured in accordance with embodiments of the present invention (e.g., guide body, guide hafts, guide body lock) can be made from any suitable material using any suitable fabrication process. Examples of suitable materials include, but are not limited to, polymeric materials and metallic materials. Examples of suitable fabrication processes include, but are not limited to, molding, machining, 3-D printing, extrusion, casting and the like.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An implanted article physical referencing apparatus, comprising:
   a guide body including a plurality of guide shaft receptacles therein, wherein a longitudinal axis of each of the guide shaft receptacles extends substantially parallel to a longitudinal reference axis of the guide body, wherein at least a portion of the plurality of guide shaft receptacles intersect each other, and wherein each of said intersecting ones of the guide shaft receptacles has a cylindrical side wall and a shoulder extending therefrom; and
a first guide shaft having a proximate end portion and a distal end portion, wherein the proximate end portion of the first guide shaft includes an exterior surface adapted for being engaged with a corresponding interior surface of a selected one of the guide shaft receptacles to constrain unrestricted relative movement between the first guide shaft and the guide body and wherein the exterior surface of the first guide shaft includes a cylindrical side wall portion including a shoulder extending therefrom that engages the shoulder of one of said intersecting ones of the guide shaft receptacles when the cylindrical side wall portion of the first guide shaft is seated in a selected one of the guide shaft receptacles for constraining axial displacement of the first guide shaft relative to the guide body.

2. The implanted article physical referencing apparatus of claim 1, further comprising:
a guide shaft lock including a guide body engaging portion and a first guide shaft engaging portion, wherein the guide body engaging portion is engaged with the guide body to constrain relative movement between the guide shaft lock and the guide body in a direction generally perpendicular to the longitudinal reference axis of the guide body and wherein the first guide shaft engaging portion is engaged with the first guide shaft to constrain relative movement between the guide body and the first guide shaft in a direction generally parallel to the longitudinal reference axis of the guide body when the first guide shaft is engaged with any of the guide shaft receptacles.

3. The implanted article physical referencing apparatus of claim 1, further comprising:
a second guide shaft having a proximate end portion and a distal end portion, wherein the proximate end portion of the second guide shaft is attached to the guide body and wherein a longitudinal axis of the second guide shaft extends substantially parallel to the longitudinal reference axis of the guide body.

4. The implanted article physical referencing apparatus of claim 1 wherein the longitudinal axis of each of the guide shaft receptacles lie on a transverse reference axis of the guide body.

5. The implanted article physical referencing apparatus of claim 4, further comprising:
a guide shaft lock including a guide body engaging portion and a first guide shaft engaging portion, wherein the guide body engaging portion is selectively engageable with the guide body to constrain relative movement between the guide shaft lock and the guide body in a direction generally perpendicular to the longitudinal reference axis of the guide body and wherein the first guide shaft engaging portion is selectively engageable with the first guide shaft to constrain relative movement between the guide body and the first guide shaft in a direction generally parallel to the longitudinal reference axis of the guide body when the first guide shaft is engaged with any of the guide shaft receptacles.

6. The implanted article physical referencing apparatus of claim 1 wherein:
a first one of the guide shaft receptacles defines a reference location guide shaft receptacle;
two or more of the other guide shaft receptacles each define a respective one of a plurality of target location guide shaft receptacles;
each of the target location guide shaft receptacles is spaced-apart from each adjacent one of the target location guide shaft receptacles; and
the reference location guide shaft receptacle is spaced away from all of the target location guide shaft receptacles.

7. The implanted article physical referencing apparatus of claim 6 wherein the longitudinal axis of each of the guide shaft receptacles lie on a transverse reference axis of the guide body.

8. The implanted article physical referencing apparatus of claim 6, further comprising:
a second guide shaft having a proximate end portion and a distal end portion, wherein the proximate end portion of the second guide shaft is engaged with the reference location guide shaft receptacle and wherein a longitudinal axis of the second guide shaft extends substantially parallel to the longitudinal reference axis of the guide body.

9. The implanted article physical referencing apparatus of claim 8 wherein:
the longitudinal axis of each of the guide shaft receptacles lie on a transverse reference axis of the guide body; and
the target location guide shaft receptacles intersect each other.

10. The implanted article physical referencing apparatus of claim 6, further comprising:
a guide shaft lock including a guide body engaging portion and a first guide shaft engaging portion, wherein the guide body engaging portion is selectively engageable with the guide body to constrain relative movement between the guide shaft lock and the guide body in a direction generally perpendicular to the longitudinal reference axis of the guide body and wherein the first guide shaft engaging portion is selectively engageable with the first guide shaft to constrain relative movement between the guide body and the first guide shaft in a direction generally parallel to the longitudinal reference axis of the guide body when the first guide shaft is engaged with any of the guide shaft receptacles.

11. A variable implant article placement guide assembly, comprising:
a guide body including a reference location guide shaft receptacle therein and a plurality of target location guide shaft receptacles therein, wherein a longitudinal axis of all of the guide shaft receptacles extends substantially parallel to a longitudinal reference axis of the guide body, wherein each of the target location guide shaft receptacles is spaced-apart from each adjacent one of the target location guide shaft receptacles, wherein the reference location guide shaft receptacle is spaced away from all of the target location guide shaft receptacles, and wherein each of the target location guide shaft receptacles comprises a stepped sidewall passage extending through the guide body;
a first guide shaft having a proximate end portion and a distal end portion, wherein the proximate end portion of the first guide shaft includes an exterior surface engaged with any selected one of the target location guide shaft receptacles to constrain unrestricted relative movement between the first guide shaft and the guide body and wherein the first guide shaft has a stepped side wall defining a shoulder that engages the stepped sidewall passage of a selected one of the target location guide shaft receptacles when engaged therein thereby defining a seated position of the first guide shaft within the selected one of the target location guide shaft receptacles; and a second guide shaft having a proximate end portion and a distal end portion, wherein the proximate end portion of the second guide shaft is engaged with the reference location guide shaft receptacle to constrain unrestricted relative movement between the second guide shaft and the guide body and wherein a longitudinal axis of the second guide shaft is the longitudinal reference axis of the guide body.

12. The variable implant article placement guide assembly of claim 11, further comprising:

a guide shaft lock including a guide body engaging portion and a first guide shaft engaging portion, wherein the guide body engaging portion is selectively engageable with the guide body to constrain relative movement between the guide shaft lock and the guide body in a direction generally perpendicular to the longitudinal reference axis of the guide body and wherein the first guide shaft engaging portion is selectively engageable with the first and second guide shafts to constrain relative movement between the guide body and the first and second guide shafts in a direction generally parallel to the longitudinal reference axis of the guide body when the first guide shaft is engaged with any of the target location guide shaft receptacles and the second guide shaft is engaged with the reference location guide shaft receptacle.

13. The variable implant article placement guide assembly of claim 12 wherein the guide shaft lock including a guide body engaging portion and a first guide shaft engaging portion, wherein the guide body engaging portion is selectively engageable with the guide body to constrain relative movement between the guide shaft lock and the guide body in a direction generally perpendicular to the longitudinal reference axis of the guide body and wherein the first guide shaft engaging portion is selectively engageable with the first and second guide shafts to constrain relative movement between the guide body and the first and second guide shafts in a direction generally parallel to the longitudinal reference axis of the guide body when the first guide shaft is engaged with any of the target location guide shaft receptacles and the second guide shaft is engaged with the reference location guide shaft receptacle.

14. The variable implant article placement guide assembly of claim 11 wherein the longitudinal axis of each of the guide shaft receptacles lie on a transverse reference axis of the guide body that extends perpendicularly through the longitudinal reference axis.

15. The variable implant article placement guide assembly of claim 11 wherein each of the guide shaft receptacles intersect each adjacent guide shaft receptacle.

16. An implanted article physical referencing apparatus, comprising:

a guide body including a plurality of guide shaft receptacles therein, wherein a longitudinal axis of each of the guide shaft receptacles extends substantially parallel to a longitudinal reference axis of the guide body, wherein at least a portion of the plurality of guide shaft receptacles intersect each other, and wherein each of said intersecting ones of the guide shaft receptacles has a side wall portion and a shoulder extending therefrom; and a first guide shaft having a proximate end portion and a distal end portion, wherein the proximate end portion of the first guide shaft includes an exterior surface adapted for being engaged with a corresponding interior surface of a selected one of the guide shaft receptacles to constrain unrestricted relative movement between the first guide shaft and the guide body and wherein the exterior surface of the first guide shaft includes a side wall portion including a shoulder extending therefrom that engages the shoulder of one of said intersecting ones of the guide shaft receptacles when the side wall portion of the first guide shaft is seated in a selected one of the guide shaft receptacles for constraining axial displacement of the first guide shaft relative to the guide body.

17. The implanted article physical referencing apparatus of claim 16, further comprising:

a guide shaft lock including a guide body engaging portion and a first guide shaft engaging portion, wherein the guide body engaging portion is engaged with the guide body to constrain relative movement between the guide shaft lock and the guide body in a direction generally perpendicular to the longitudinal reference axis of the guide body and wherein the first guide shaft engaging portion is engaged with the first guide shaft to constrain relative movement between the guide body and the first guide shaft in a direction generally parallel to the longitudinal reference axis of the guide body when the first guide shaft is engaged with any of the guide shaft receptacles.

18. The implanted article physical referencing apparatus of claim 16 wherein:

a first one of the guide shaft receptacles defines a reference location guide shaft receptacle;

two or more of the other guide shaft receptacles each define a respective one of a plurality of target location guide shaft receptacles;

each of the target location guide shaft receptacles is spaced-apart from each adjacent one of the target location guide shaft receptacles; and the reference location guide shaft receptacle is spaced away from all of the target location guide shaft receptacles.

19. The implanted article physical referencing apparatus of claim 18 wherein the longitudinal axis of each of the guide shaft receptacles lie on a transverse reference axis of the guide body.

* * * * *